United States Patent [19]

McFarlane

[11] Patent Number: 4,908,021
[45] Date of Patent: Mar. 13, 1990

[54] FLASHBACK CHAMBER FOR CATHETER ASSEMBLY

[76] Inventor: Richard H. McFarlane, 2571 Kaneville Rd., Geneva, Ill. 60134

[21] Appl. No.: 832,134

[22] Filed: Feb. 24, 1986

Related U.S. Application Data

[63] Continuation of Ser. No. 621,107, Jun. 15, 1984, abandoned.

[51] Int. Cl.⁴ .............................................. A61M 5/00
[52] U.S. Cl. ..................................... 604/168; 604/900
[58] Field of Search ............................... 604/164–169, 604/122, 900

[56] References Cited

U.S. PATENT DOCUMENTS 4,016,879  4/1977  Mellor ........................... 604/168 X
4,108,175  8/1978  Orton ................................ 604/168
4,200,096  4/1980  Charvin ......................... 604/168 X
4,292,970  10/1981  Hession .............................. 604/164
4,365,630  12/1982  McFarlane ......................... 604/168

Primary Examiner—Dalton L. Truluck
Attorney, Agent, or Firm—John Cyril Malloy

[57] ABSTRACT

A flashback chamber for a catheter assembly including a main body portion having a cavity formed therein which is structured to include a path of fluid flow along its length defined by a plurality of sequentially disposed chambers separated, at least in part, by transversely located ribs. The path of fluid flow is at least partially defined by a plurality of ports formed at opposite ends of the spaced apart ribs. An air only permeable vent structure is located at the end of the path of fluid flow so as to properly vent air forced from the cavity as blood from the catheter assembly successively fills the sequentially disposed chambers.

15 Claims, 2 Drawing Sheets

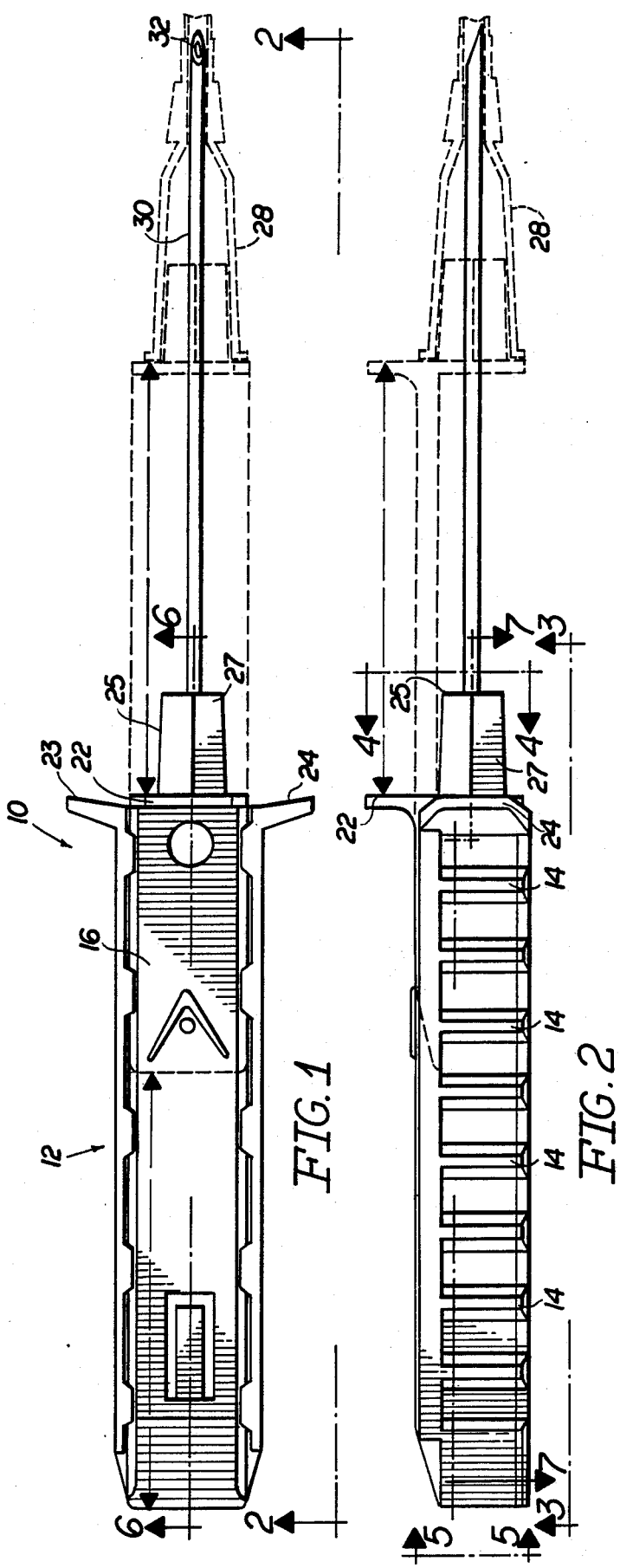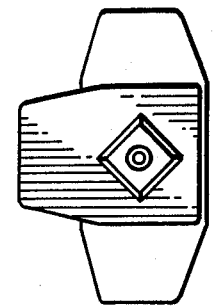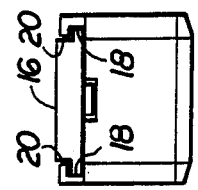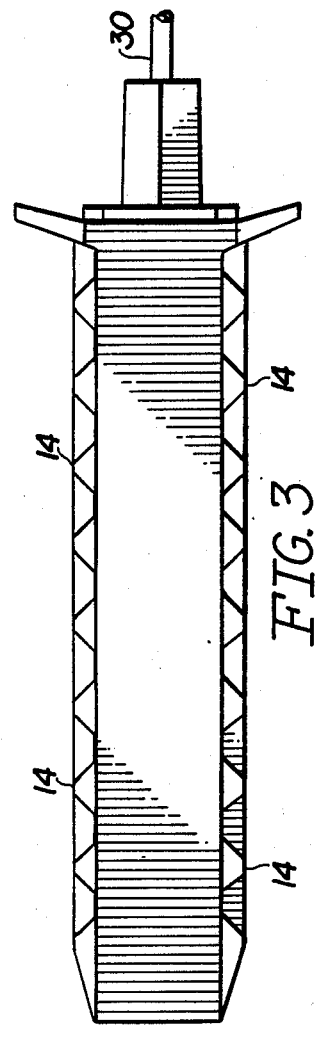

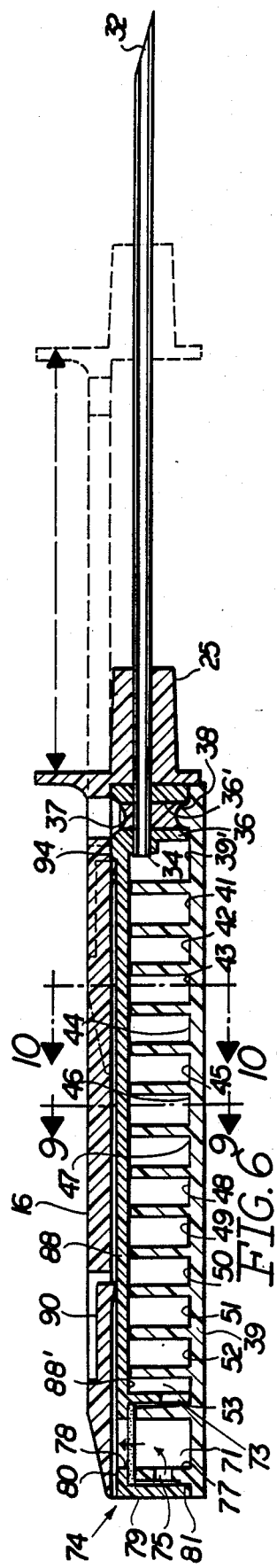
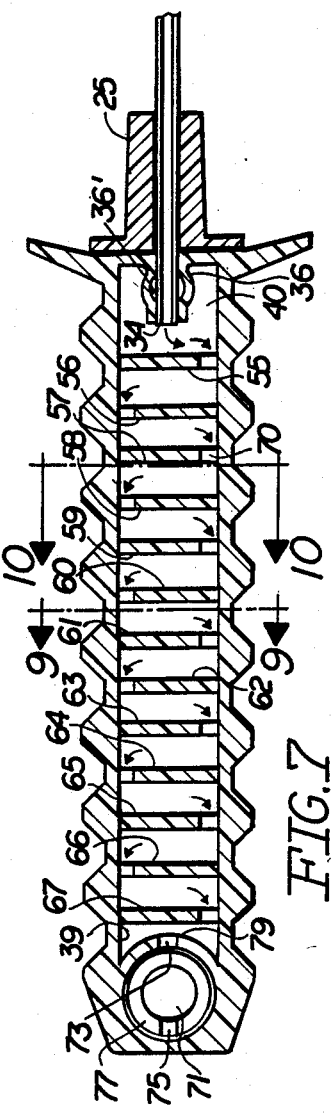
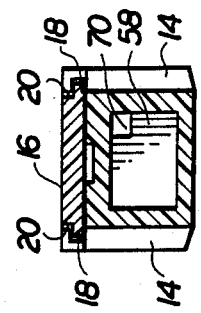
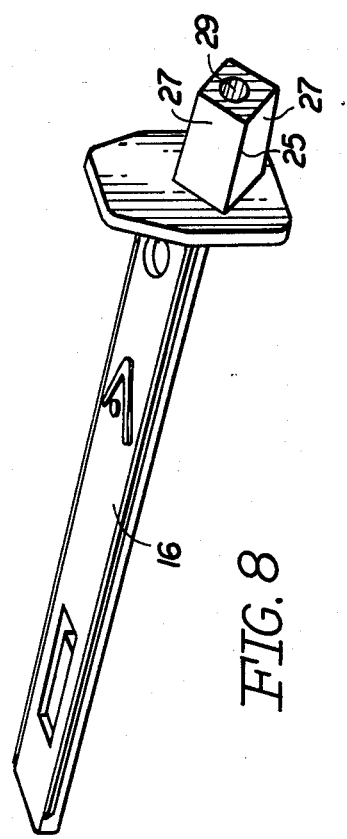

FLASHBACK CHAMBER FOR CATHETER ASSEMBLY

This is a continuation application of copending application Ser. No. 621,107, filed June 15, 1984, now abandoned.

BACKGROUND OF THE INVENTION

1. Field of the Invention:

A flashback chamber specifically structured to observe the inflow of blood from a catheter applied to a patient's blood vessel wherein the incoming blood flows evenly and successively along a plurality of chambers defined on the interior cavity of the flashback chamber, thereby insuring proper placement of the catheter assembly within the blood vessel.

2. Description of the Prior Art:

In the proper placement of a catheter assembly, it is important for medical personnel to know when the needle and surrounding catheter is properly placed within the blood vessel of the patient being administered. When properly positioned, blood flows continuously through a hollow needle. This blood will continue to flow into any receiving chamber or cavity which allows the user of the subject structure to visually observe the relative rate of blood flow. If the flow is continuous, the user knows that the tip of the needle is properly positioned in a vein or artery and the catheter, coaxially disposed about the penetrating needle, is ready for subsequent advancement into the vein in which the needle tip has been properly positioned.

While visual observation of incoming blood flow is recognized as an efficient and proper means of determining whether the sharpened tip of a needle is positioned within the blood vessel of the patient, there is a need in the medical profession for what may be termed a flashback chamber. This flashback chamber, ideally, should be properly structured to observe the incoming blood flow as it passes from the needle into a chamber or cavity. Such a structure is clearly set forth in U.S. Pat. No. 4,365,630. The present invention is directed towards an improvement of the flashback chamber for catheter as disclosed in the above set forth U.S. patent and relates to structural modifications of a cavity disposed within the hollow interior of the main body portion as well as the vent means associated with allowing of venting or passge of air from the interior of the cavity once the cavity is being filled with the incoming flow of blood.

SUMMARY OF THE INVENTION

The flashback chamber of the present invention is, as generally set forth above, designed for use in combination with a catheter wherein the catheter hub is disposed in coaxial, jacketed and slidable relation about a hollow needle. The distal end of the needle is sharpened to facilitate penetration into the blood vessel of the patient and the proximal end is mounted on the interior of a main body portion and in fluid communication therewith.

The main body portion includes a cavity located on the interior thereof and structured to include a path of fluid flow for liquid, such as blood which passes through the hollow needle, from the proximal end thereof into the cavity and along the length thereof for visual observation. The cavity as well as the path of fluid flow is further defined by a plurality of successively disposed chambers sequentially positioned relative to the path of fluid flow such that the inflow of blood passs sequentially from the first-most chamber to the remaining chambers along the length of the cavity and the path of fluid flow defined thereby.

The cavity is closed or sealed along its length by an elongated member fixedly attached to the cavity along the length thereof. A vent means is located adjacent one end of the cavity at the substantial end of the path of fluid flow and is specifically structured to be gas permeable thereby allowing venting or forcing of air from the interior of the cavity as the inflowing blood fills the cavity from the first-most chamber sequentially towards the end of the cavity.

More particularly, the vent means includes a disk-like element which is formed from a material which is permeable to gas or air but which does not allow the passage of liquid therethrough. The vent means further includes an aperture formed in the elongated member and located immediately adjacent the vent disk and in aligned registry therewith. Air being vented from the cavity, upon the inflow of blood, passes through the vent disk and out the aperture to the exterior of the cavity.

A slidable member is movably mounted to slide or travel parallel to the longitudinal axis of both the cavity and the hollow needle extending from the front end of the main housing portion. This slidable member includes an upstanding flange at its front-most end which is disposed in substantially abutting relation with the slidably mounted catheter fixed in coaxial relation about the hollow needle.

In operation, the sharpened end of the hollow needle is passed into a blood vessel of the patient being administered. Blood from the blood vessel, when the sharpened tip is properly positioned, passes continuously and freely through the hollow needle and into the cavity, along its length and sequentially through the plurality of chambers. If the sharpened tip of the needle is properly placed, the blood flow will be continuous along the path of fluid flow and successively along the sequentially disposed chambers. The chambers are interconnected in fluid communication with one another by a plurality of ports disposed to define, along with the structure and disposition of the individual chambers, a substantially serpentine configuration of the path of fluid flow thereby defining such path to have a length effectively longer than the longitudinal dimension of the cavity itself. Proper visual observation is thereby provided by the user of the assembly as the inflowing blood sequentially fills the plurality of chambers along the length of the cavity. The air preceding the flow of incoming blood is also forced along the path of fluid flow out through the vent means from the plurality of chambers.

An important structural feature of the present invention is the provision of the slidable member serving to move substantially parallel to the longitudinal axis of the hollow needle and in abutting relation to an end thereof so as to force the catheter from its jacketed positon about the needle into advancement within the blood vessel initially penetrated by the sharpened tip of the hollow needle.

The invention accordingly comprises the features of construction, combination of elements, and arranement of parts which will be exemplified in the construction hereinafter set forth, and the scope of the invention will be indicated in the claims.

BRIEF DESCRIPTION OF THE DRAWINGS

For a fuller understanding of the nature of the present invention, reference should be had to the following detailed description taken in connection with the accompanying drawings in which:

FIG. 1 is a top plan view of the flashback chamber structure of the present invention with the catheter and the advancement thereof represented in broken lines.

FIG. 2 is a side plan view along line 2—2 of FIG. 1.

FIG. 3 is a bottom view along line 3—3 of FIG. 2.

FIG. 4 is an end view of the main body portion of the flashback chamber structure along line 4—4 of FIG. 2.

FIG. 5 is an end view along line 5—5 of FIG. 2.

FIG. 6 is a sectional view along line 6—6 of FIG. 1 showing the interior structura details of the main body portion of the subject flashback chamber.

FIG. 7 is a sectional view taken along line 7—7 of FIG. 2 showing the path of fluid flow as inflowing blood is delivered to the interior cavity of the housing portion and passes along the sequentially disposed chambers which in part define the path of fluid flow.

FIG. 8 is an isometric view of a slidable member which forces advancement of a catheter into the blood vessel and from its surrounding, jacketed position about the hollow needle.

FIG. 9 is a sectional view along line 9—9 of FIGS. 6 and 7.

FIG. 10 is a sectional view along line 10—10 of FIGS. 6 and 7.

Like reference characters refer to like parts throughout the several views of the drawings.

DETAILED DESCRIPTION OF THE PREFERRED EMBODIMENT

As shown in FIGS. 1 through 3, the flashback chamber structure of the present invention is generally indicated as 10 and includes a main body portion generally indicated as 12. Finger grip means are located on the oppositely disposed, spaced apart lateral sides of the main body portion 12 and include a plurality of transversely oriented flutes 14 integrally formed on the exterior surface of the lateral sides in spaced apart relation to one another. The top, outermost portion of the main body portion 12 includes a slidable member 16 (see FIG. 5) having outwardly extending side edges 18 extending along the length thereof and disposed to be slidably received within longitudinally extending grooves 20 extending upwardly from the respectively positioned lateral sides to which the flutes 14 are formed. Further, the slidable member 16 has an upwardly extending flange 22 disposed adjacent the frontmost portion of the main housing portion 12 when the slidable member is in its "closed" position as shown in solid lines in FIGS. 1 through 3, 6 and 7. Similarly, and as part of the finger grip means set forth above, the lateral sides include outwardly extending flange elements 23 and 24.

The slidable member further includes a tapered nose portion 25 having a plurality of faces 27. The nose portion 25 is dimensioned and structured to fit within the hub 28 (represented in broken lines) of a standard I.V. catheter wherein such hub 28 is disposed in abutting relation with the upstanding flange member 24.

A hollow interior needle 30 includes a distal sharpened end or tip 32 extending outwardly and away from the main body portion 12. The proximal end 34 is disposed in fluid communication with a cavity disposed on the interior of the main housing portion 12 and in direct fluid communication with a first chamber 40 of a plurality of successive chambers 40 through 53. The nose portion 25 further includes a mounting aperture 29 through which the proximal end 34 of the needle 30 is disposed for its communicating disposition with the interior of the cavity within main body portion 12. In order to connect the needle 30 in the manner described, the proximal end 34 is disposed through aperture 29 such that it is positioned in transverse relation to web extension 36 integrally connected to extend downwardly from inside surface 88' of elongated member 88. Proximal end 34 is also disposed transverse to central channel 36' within web extension 36. In order to secure proximal end 34 in place (see FIGS. 6 and 7) adhesive or like binding material 37 is disposed within channel 36' and allowed to harden about the proximal end 34 as shown. The lower end of channel 36' is closed through positioning therein of projection 35 integrally secured to and extending upwardly from inner surface 39' of bottom side 39 of the body portion 12.

Further, with regard to the interior of the main body portion 12, each of the successively disposed chambers 40 through 53 are separated by a plurality of spaced apart, substantially parallel ribs 55 through 67 integrally secured to and extending upwardly from inner surface 39' of bottom 39. The path of fluid flow is defined by these chambers, in part, and by a plurality of ports each of which is indicated by the same numeral 70. Each port 70 is integrally formed adjacent one end of the respective ribs 55 through 67. More specifically, the ports 70 are located in oppositely disposed ends of successively disposed ribs in order to define the path of fluid flow as having a substantially serpentine configuration as generally indicated by the directional arrows of FIG. 7.

Also, the placement of the ports are clearly indicated with reference to FIG. 10 wherein each of the ports 70 may be located in an upper or corner adjacent position in the respective rib in which it is formed such as 61 and 58. By virtue of the disposition, configuration and dimension of each of the ports 70, the blood passes along at least a portion of the length of the path of fluid flow having a substantially reduced cross-sectional dimension such that its visual observation can be accomplished.

Other structural features of the present invention include the provision of a vent means generally indicated as 74 including a disk element 76 formed from an air or gas only permeable material specifically structured to prevent the passage of liquid therethrough. An aperture means 78 is formed in an elongated member 88 directly above and in aligned relation with the vent disk 76 so as to allow passage of air through the disk 76. Air passing through disk 7 and aperture means 78 travels along the space 80 between the slide member 16 and the elongated member 88 defining a top side of the main body portion 12, (FIG. 6) to the exterior of the cavity and main body portion 12. Further structural features of the vent means 74 includes a first cylindrically formed sleeve 77 extending upwardly from the inside surface 39' of the bottom side 39 the main body portion 12. The disposed on the interior of and in concentrically surrounded relation by a second sleeve 79 integrally formed and extending downwardly from the elongated top side 88. The first and second sleeves are relatively dimensioned so as to be brought into frictional engagement with one another as at the lower peripheral engaging surfaces 81 (FIG. 6). Air is vented by exiting the last chamber 53 through an opening 73 formed in the second sleeve 79. A second opening 75 is formed in the first sleeve 77 and allows passage of the vented air into the venting chamber 71 located within the center of the first sleeve 77. From this venting chamber 74, the air to be vented passes through the venting disk 76, aperture means 78 and spacing 80 to the exterior of the cavity and main body portion 12 in accordance with the directional arrows as shown in FIG. 6.

In operation, the sharpened distal end or tip 32 of the needle 30 is positioned within the blood vessel of a patient. When properly positioned, blood flow passes continuously through the hollow needle and into the first of the plurality of chambers 40 through proximal end 34 of the needle. The blood flow then continues to fill the cavity by passing sequentially through the successively disposed chambers 41, 42, 43, 44, etc. towards the rearmost end of the main housing portion 12 and the vent means 74. The blood may not entirely fill the entire length of the inner cavity and all of the plurality of chambers. However, as the blood is inflowing the air contained within these chambers is forced from the front to the rear of the cavity along the path of fluid flow through the various ports 70 and the successively disposed chambers. Such air is vented out from the vent means 74 as explained above and blood flow is allowed to continue to fill the cavity. When the user of the structure observes such continuous and free flow of incoming blood into the flashback chamber structure, the slidable member 16 is advanced forwardly (see broken lines in FIGS. 1, 2 and 6) until depending stop means 90 engages portion 94 of the top side 88. The stop means 90 and the portion 94 are disposed in interruptive relation to one another to limit the forward advance of the slidable member 16 along the length of the needle 30 towards the sharpened distal end 32. The catheter 28' is thereby advanced from its coaxial, jacketed relation to the needle 30 and into the blood vessel in the conventional manner.

It is therefore to be understood that the following claims are intended to cover all of the generic and specific features of the invention herein described, and all statements of the scope of the invention which as a matter of language, might be said to fall therebetween.

Now that the invention has been described,

What is claimed is:

1. An improved flashback structure of the type primarily designed for use with a catheter, said structure comprising:
   (a) a main body portion structured to include an elongated cavity on the interior thereof, said cavity defining a path of fluid flow extending along the length thereof,
   (b) said main body portion comprising a bottom side and a top side disposed in spaced, parallel relation to one another and extending the length of said cavity in enclosing relation to said cavity and said path of fluid flow therein,
   (c) a slidable member having an elongated configuration and movably mounted on said main body portion in parallel relation to said top side and disposed in overlying relation to said top side and further disposed to define a space between said slidable member and said top side,
   (d) an elongated hollow needle secured to and extending outwardly from said main body portion and including a sharpened distal end, said needle including a proximal end mounted in fluid communication with said path of fluid flow,
   (e) a chamber maze formed in said cavity and comprising a plurality of successively disposed chambers positioned along the length of and at least partially defining said path of fluid flow; said plurality of chambers extending from one end of said cavity adjacent said proximal end of said needle to a distal end of said cavity,
   (f) a vent means for venting air from said cavity and including a vent chamber disposed at said distal end of said cavity and defining an endmost chamber of said plurality of chambers and disposed and structured on said main body portion for fluid communication with said path of fluid flow,
   (g) said vent means comprising a vent disk formed of gas only permeable material, whereby liquid may not pass therethrough, said disk element mounted in said vent chamber in fluid communication with said path of fluid flow,
   (h) said vent means further comprising an aperture means integrally formed in said top side in aligned and fluid communicating relation with said disk element, said aperture means disposed to establish fluid communication between said vent disk and said space between said slidable member and said top side, said space disposed in communicating relation with the exterior of said main body portion,
   (i) said vent means cooperatively structured and disposed relative to said cavity to force air to be vented from said cavity successively through said vent chamber, said vent disk, said aperture means and said space between said slidable member and said top side, as blood enters said chamber maze at said one end of said cavity.

2. A structure as in claim 1 wherein said plurality of chambers are at least partially separated by spaced apart, substantially parallel ribs each disposed in transverse relation to the longitudinal axis of said cavity and along the length thereof.

3. A structure as in claim 2 wherein said path of fluid flow is at least partially defined by a plurality of ports, each of said ports being formed in one of said ribs, each of said ribs including said respective port integrally formed therein and along an end which is oppositely disposed to the next successively disposed rib, said flow path thereby defined to include a substantially serpentine configuration along the length thereof and said cavity.

4. A structure as in claim 1 wherein said device includes a catheter snugly and slidably jacketing said needle along the length thereof to the sharpened distal end and said catheter extending from said slidable member on said main body portion and being connected thereto for advancing said catheter slidably and in coaxial relation with said needle.

5. A structure as in claim 1 wherein said member includes a downwardly extending front wall including a forwardly projecting tapered nose portion provided with a through hole to permit free longitudinal coaxial movement of said slidable member relative to said needle.

6. A structure as in claim 5 wherein said nose portion is sized and configured for engagement within an open rear end of a conventional I.V. catheter hub.

7. A structure as in claim 1 wherein said slidable member includes stop means formed thereon in depending, spaced relation to an undersurface thereof, said stop means disposed in interruptive relation with a front-most portion of said body portion when said slidable member extends outwardly from said body portion in overlying relation to said needle.

8. A structure as in claim 1 wherein an outer surface of said main body portion comprises finger grip means including a plurality of flutes oriented in spaced apart parallel relation to one another along the length of both lateral walls of said body portion and transverse relation to the longitudinal axis of said body portion.

9. A structure as in claim 8 wherein each of said lateral walls terminate in oppositely, outwardly extending flanges mounted adjacent a front-most end of said body portion.

10. A structure as in claim 1 wherein said slidable member terminates at a front end thereof in an upwardly extending flange adjacent a front end of said body portion.

11. A structure as in claim 1 wherein said vent means comprises a first sleeve integrally formed in said vent chamber and including an open top end, said vent disk mounted across said top end in covering relation thereto and disposed in substantially aligned, directly communicating relation with said aperture means, said first sleeve structured and configured for fluid communication with said path of fluid flow, whereby air forced from said cavity passes through said first sleeve, said vent disk, said aperture means and said space to atmosphere.

12. A structure as in claim 11 wherein said first sleeve includes a longitudinal dimension sufficient to maintain said vent disk being disposed in covering, interconnecting relation with both said open top end of said first sleeve and said aperture means.

13. A structure as in claim 11 wherein said vent means further comprises said first sleeve extending upwardly from an inner surface of said bottom side within said vent chamber and a second sleeve formed in said vent chamber and extending downwardly from an inner surface of said top side, said first and said second sleeve disposed in substantially concentric relation to one another, said vent chamber including an apertured construction defining fluid communication between said path of fluid flow and an interior of said first sleeve and said vent disk.

14. A structure as in claim 13 wherein said vent disk is mounted on the interior of said second sleeve and in covering and interconnecting relation with both said open top end of said first sleeve and said aperture means.

15. A structure as in claim 1 wherein said slidable member and said top side are both formed from a material through which blood said cavity can be viewed.

* * * * *